United States Patent [19]
Shine et al.

[11] Patent Number: 6,084,392
[45] Date of Patent: Jul. 4, 2000

[54] ELECTRODE ASSEMBLY

[76] Inventors: Thomas Adam Shine, 220 Lawrence St. No. 3, Newhaven, Conn. 06511; Ian Basil Shine, 444 Central Park West, New York, N.Y. 10025

[21] Appl. No.: 09/101,033
[22] PCT Filed: Dec. 27, 1996
[86] PCT No.: PCT/GB96/03241
   § 371 Date: Aug. 4, 1998
   § 102(e) Date: Aug. 4, 1998
[87] PCT Pub. No.: WO97/24600
   PCT Pub. Date: Jul. 10, 1997

[30] Foreign Application Priority Data

Dec. 29, 1995 [GB] United Kingdom .................. 9526652

[51] Int. Cl.$^7$ ................................................. G01N 15/12
[52] U.S. Cl. ...................... 324/71.1; 324/71.4; 324/450; 204/409; 377/12
[58] Field of Search ................... 324/71.1, 71.4, 324/444, 450; 204/400, 409, 411, 412; 377/11, 12; 73/1.02, 105

[56] References Cited

U.S. PATENT DOCUMENTS

| | | | |
|---|---|---|---|
| 3,648,158 | 3/1972 | Parker | 324/450 |
| 3,714,565 | 1/1973 | Coulter et al. | 324/71.1 |
| 3,771,058 | 11/1973 | Hogg | 324/71.1 |
| 4,395,676 | 7/1983 | Hollinger et al. | 324/71.4 |
| 4,438,390 | 3/1984 | Hogg | 324/71.1 |
| 4,484,134 | 11/1984 | Halloran | 324/71.1 |
| 4,627,893 | 12/1986 | Cormier et al. | 204/409 |
| 5,007,296 | 4/1991 | Hukuhara | 324/71.4 |

FOREIGN PATENT DOCUMENTS

| | | |
|---|---|---|
| 0 246 011 | 11/1987 | European Pat. Off. . |
| 0 384 789 | 8/1990 | European Pat. Off. . |

*Primary Examiner*—Diep N. Do
*Attorney, Agent, or Firm*—Burns, Doane, Swecker & Mathis, L.L.P.

[57] ABSTRACT

An electrode assembly (1) for resistive pulse spectroscopy comprises two flat electrodes (3) substantially equal in size and shape and supported in face-to-face, parallel relationship to one another, and a plate-like fluid-tight insulator (2) positioned between electrodes and extended beyond the periphery of the electrodes with the electrodes (3) being fixed to the insulator (2). Each electrode has a hole (4) extending through the electrode in a central region thereof (4), the holes (4) of the two electrodes (3) being aligned with one another. The insulator (2) having a preformed aperture (16) therein which is located substantially centrally with respect to the holes (4) in the electrodes (3) and has a smaller diameter than the holes, the aperture (16) being located such as to allow a flow of liquid to pass therethrough and through the holes in the electrode.

19 Claims, 2 Drawing Sheets

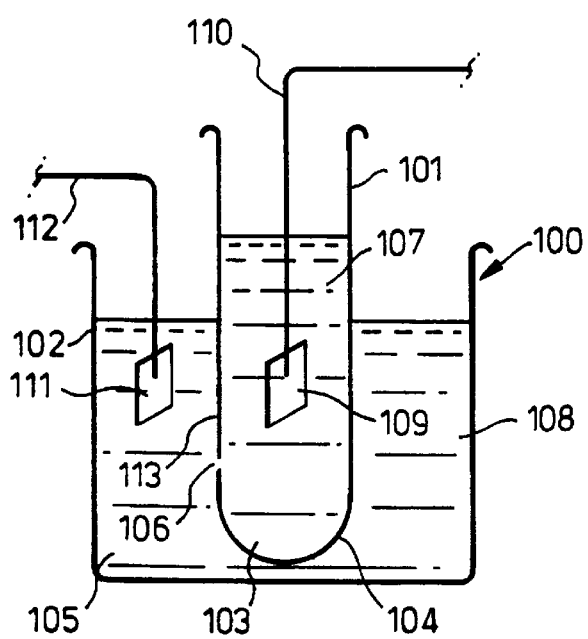
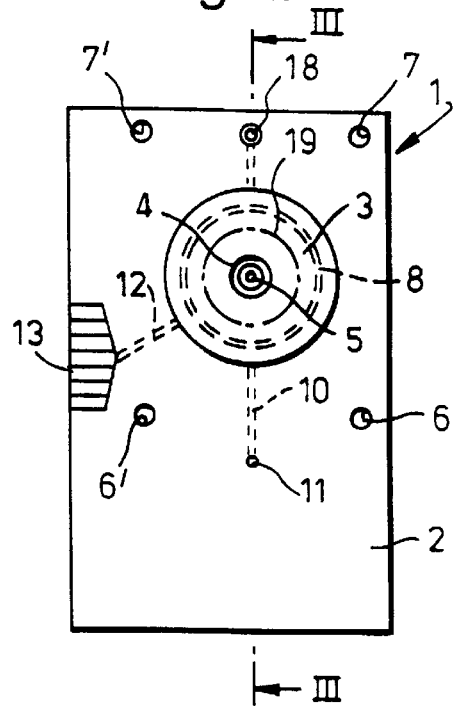
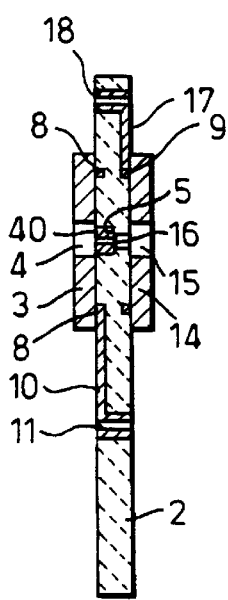
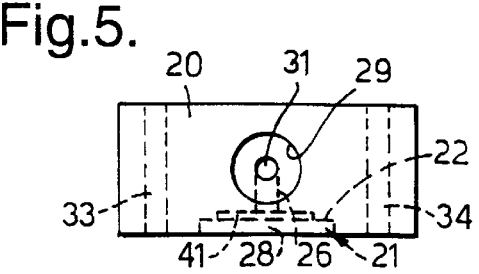

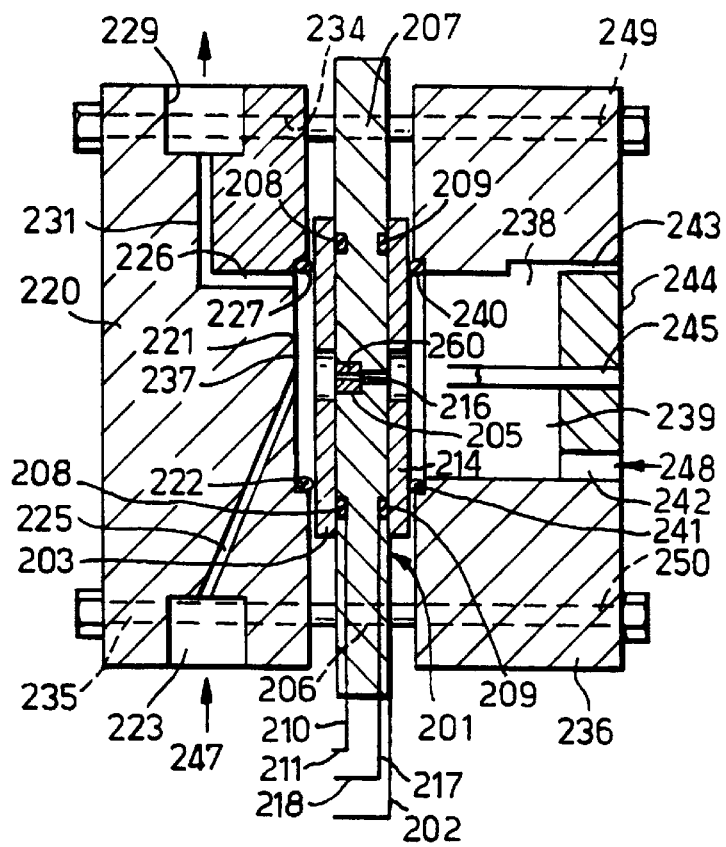
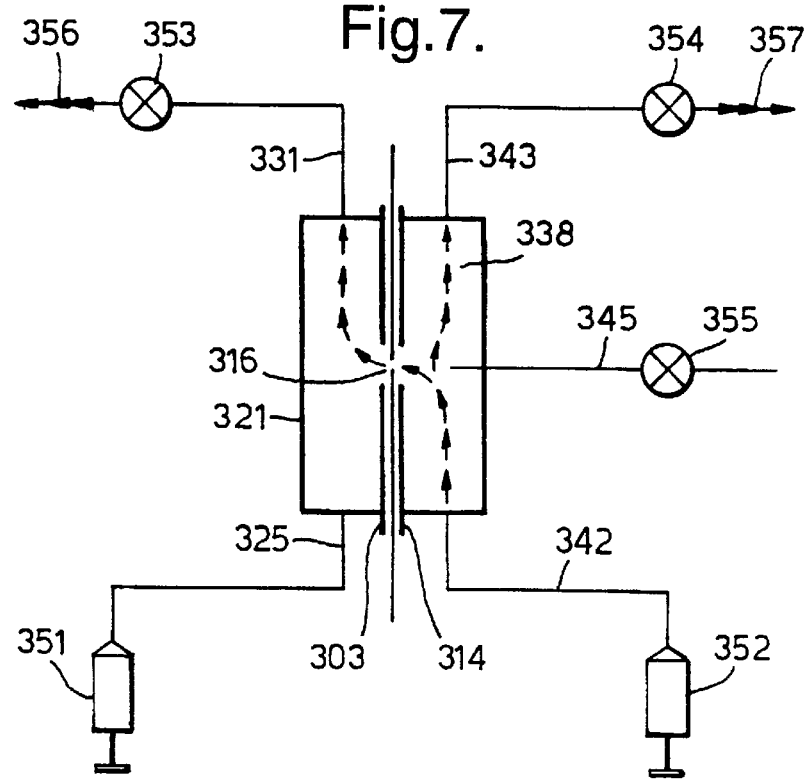

ELECTRODE ASSEMBLY

TECHNICAL FIELD

The present invention relates to an electrode assembly for use in apparatus for carrying out electronic particle sizing, particularly for sizing of blood cells.

BACKGROUND ART

The automated testing of blood samples has become an important part of many medical investigations. Automated instruments' speed and ease of use has made them the preferred method of producing a complete blood count (CBC) in hospital laboratories, despite the errors and inaccuracies induced by the method. The errors usually do not cause much problem in routine testing, but there has recently been a growing concern in the literature about incorrect cell sizing due to the automated methods.

The specification describes novel mechanical methods of minimizing the errors produced by existing technology and describes ways to improve the accuracy and resolution of current technology, in particular when used with red blood cells or whole blood samples.

Automated particle counters typically use a sensor which detects particles in a restricted flow, producing a measure of particle size and count for each particular type of particle. The sensor usually detects a change in an electrical field, an alteration in the light scatter from a laser, a change in the magnetic field density or magnetic flux, or changes in the optical, acoustic or other physical properties of the cells or cell suspension and/or suspending liquid. Whatever type of sensor is used, it produces a signal which is a product of a particle's size, shape, trajectory, number and other properties, some of which may be measured concomitantly. Electronic particle counters which use a direct or alternating current as a method to detect particles can be referred to as electronic particle sizing devices (hereinafter referred to as EPS), and produce a characteristic change in voltage or current, usually recorded as a voltage pulse as a particle passes through a restriction (aperture).

Electronic particle sizing relies on two electrodes suspended in a conducting solution which are isolated from each other except for a single conducting channel which is traversed by cells or other small particles in suspension. As a particle passes through the channel (aperture) measurable physical characteristics of the channel temporarily change in proportion to the particle's size. By measuring the properties of these changes, the size and concentration of particles is determined. This is performed on red cells, white cells and platelets and any free cell suspension and may be combined with stains or other techniques to further differentiate the cells by any means (i.e. optically, NMR etc).

In an ideal system, the size of a particle passing through the sensor would be described exactly by the amplified signal. However, due to theoretical limits and practical limitations of the current technology, the signal degrades before it arrives at the input to the amplifier. Noise in the system is induced by procedural errors (incomplete mixing, ignoring the sample pH, ignoring particle shape, etc) and from the physical design of the instrument (noise pick-up from long cables, impedance from the cables, poor electrode design etc) and inherent noise sources described by physical laws such as Johnson noise (white noise).

With the existing electrode design of EPS apparatus, the electrical field created by the electrodes passes extensively into the fluid body. As cells approach or exit the aperture they distort the electrical field which disturbs the charge density inside and around the aperture and degrades the electrical signal.

In existing apparatus, both sides of an electrode are exposed to electro magnetic interference (EMI). The pick up of EMI by the electrodes acting as antennae can lead to noise in the signal thereby reducing the system's sensitivity. Furthermore, since the electrodes are suspended in the liquid they are spaced at some distance from the aperture. This requires the surface area of the electrodes to be relatively large, which again increases the EMI pick up and makes the electrodes expensive in terms of materials. Further noise in the circuit is created by mechanical pick up from physical movement of the electrodes, which is inherent and cannot be prevented since the electrodes are freely suspended in the liquid.

With the existing electrode design, the electrical connections from the amplifier to the electrodes tend to be relatively long and this creates additional noise from the long signal paths. It is well known that the distance between the electrodes and the amplifier is particularly significant in increasing noise at this critical point in the circuit.

Generally, part of the leads connected to the electrode are submersed or at least exposed to the liquid, requiring them to be made of the same, expensive noble metal as the electrode itself.

A further problem with the existing apparatus is that it is laborious to clean the electrodes and the aperture. Each component must be removed from the apparatus independently to be cleaned. In practice this is often not done because it is too onerous. EP-A-0,246,011 describes a particle counter in which the electrodes are integrally formed on a sapphire wafer in which an aperture is located. A silicon layer is formed vitaxially on one side of the sapphire wafer and integrated circuits formed on a silicon layer using conventional photolithographic techniques. The aperture is formed by drilling a hole in the sapphire wafer. The piece of sapphire required for this is prohibitively expensive.

The present invention seeks to solve the above mentioned problems and confers additional benefits by providing an electrode assembly which has excellent performance, is easy to remove and replace and service and is simple to incorporate with other electronic devices into the apparatus.

DISCLOSURE OF INVENTION

According to a first aspect of the present invention, an electrode assembly comprises:

two flat electrodes supported in face to face relationship to one another, a plate like fluid type insulator positioned between the electrodes with the electrodes being fixed to the insulator, each electrode having a hole extending through the electrode, the holes of the two electrodes being aligned with one another, in which the insulator has a cavity which receives an initially separate element having an aperture preformed therein which has a smaller diameter than the said holes, the aperture being located such as to allow a flow of liquid to pass therethrough and through the holes in the electrode, and in which the electrodes are each joined to the insulator at the hole periphery by a fluid tight seal.

The insulator on which the electrodes are carried is generally formed of a substrate such as is used in printed circuit board (PCB) manufacture. It generally extends beyond the external periphery of the electrodes. It is possible, indeed, for the insulator to be formed by an area of a printed circuit board which has leads and connectors for other components of the electrical circuitry. Alternatively the insulator can be formed of a ceramic, to which the electrodes are attached or formed from inert metallic glazes.

The electrode assembly is generally provided as a unit which can be removed from and replaced into an EPS apparatus.

According to a second aspect of the present invention, a measuring section of an EPS apparatus comprises an electrode assembly of the present invention in combination with:

an inlet side fluid chamber, one wall of which is formed by one of the electrodes and the interior of which is in fluid communication with the aperture, an inlet conduit leading into the inlet side fluid chamber, a suspension waste conduit leading out of the inlet side fluid chamber, an outlet side fluid chamber, one wall of which is formed by the other of the electrodes and the interior of which is in fluid communication with the aperture, a contact fluid conduit leading into the outlet fluid chamber, a contact fluid waste conduit leading out of the outlet fluid chamber, and a measured suspension waste conduit leading out from the outlet side fluid chamber.

The inlet side fluid chamber has one wall which is formed by one of the electrodes, which can be termed the inlet side electrode. A suspension to be tested is directed into the inlet side fluid chamber through the inlet conduit. A proportion of the suspension passes through the aperture into the outlet side fluid chamber. The rest of the suspension passes out of the inlet fluid chamber through the suspension waste conduit. The inlet side fluid chamber is, for instance, formed as a recess formed in one side of a block, with the inlet and waste conduits being formed as passageways leading through from other sides of the block into the recess. The side of the block in which the recess is formed can be positioned against the inlet electrode, so as to form the inlet side fluid chamber.

Usually a fluid tight sealing gasket is provided between the face of the block having the fluid chamber forming recess and the electrode. The gasket is, for instance, retained in a seat on the block. The gasket forms a seal against the electrode itself, so that the inlet electrode has a larger area than the open area of the recess of the block surrounded by the gasket.

In a similar fashion, the outlet side fluid chamber may be formed by a recess formed in one side of a block, with inlet, outlet and waste conduits formed from passageways leading from other faces of the block to the recess. A gasket may be used to form a fluid tight seal between the face of the block and the electrode.

Preferably the open areas of blocks forming inlet side and outlet side fluid chambers are of substantially the same size and shape and are aligned on opposite sides of the electrode assembly. The blocks bear against the two electrodes at sealing gaskets arranged opposite one another so that there is no bending induced in the electrode assembly.

In the present invention the electrodes may be made of an inert conductor, usually a metal, such as gold or, preferably, platinum. The electrodes are preferably each formed of a thin layer of the metal. They may be formed by adhering a preformed foil onto the insulator surface. Foils are usually between 25 and 100 $\mu$m thick. The electrodes may alternatively be made by coating metal onto the insulator to form a film using a suitable deposition technique. Such techniques may be those used for forming thick or thin films or by electroplating or electroless plating. Deposited coatings are typically from a few atoms thick to 25 $\mu$m thick.

The insulator is generally between 10 $\mu$m and 5 mm thick, so that the electrodes are separated from one another by this distance. Preferably the thickness is in the range 0.5 to 3.0 mm.

The holes in the centre of the electrodes are preferably circular. The selection of a suitable diameter depends primarily on the outer diameter of the component bearing the aperture, if a separate component is used. With this limitation, the diameter should be as small as possible and suitable diameters have been found to be in the range 0.5 to 10 mm. The aperture within the insulator is approximately concentric with the holes and may be formed by a standard synthetic sapphire or ceramic component having a central aperture, the component being positioned and fixed within a counterbored cavity formed in the body of the insulator. The aperture preferably has an internal diameter in the range of 40 to 160 $\mu$m. Sapphire components having such apertures are available commercially and choice of an appropriate internal and external diameter and shape component depends upon the size of particle to be measured, the ease of handling during assembly etc. A person skilled in the art can select an appropriate component for the particle to be measured.

The area of the electrodes exposed to inlet fluid and outlet fluid is preferably in the range 5 mm$^2$ to 1000 mm$^2$. The external periphery of the area of the electrode exposed to the fluid is generally circular in shape.

The volume of fluid in the inlet side aperture, that is formed of sample suspension to be tested, can be kept relatively low, to minimise the volume of test suspension used and to avoid mixing the moving stream of suspension at the aperture whilst still allowing electrical contact to be achieved. For instance the volume of the inlet side fluid chamber may be less than 1 ml, for instance less than 500 $\mu$l, down to 100 $\mu$l or lower. The recess in the block forming the inlet side fluid chamber therefore has an average depth between 100 and 1000 $\mu$m, for instance around 500 $\mu$m or less.

A feature of one embodiment of the present invention which optimises liquid flow characteristics through the aperture is the provision of a measured suspension removal conduit which is a tube having a mouth positioned in the outlet chamber close to the aperture and means for reducing the pressure at the end of the tube distant from the mouth. The tube is preferably coaxial with the aperture. The reduced pressure in the tube as compared to the liquid in the outlet side fluid chamber results in particles having passed through the aperture being quickly removed from the outlet side fluid chamber and thus from the field in the neighbourhood of the aperture through the conduit to waste. This minimises disturbances of the field by the particles. Axial alignment of the tube and the aperture encourages the particles to flow through the centre of the aperture, where the velocity of the liquid is fastest and the best pulses are produced.

BRIEF DESCRIPTION OF DRAWINGS

The invention is further illustrated in the accompanying drawings in which:

FIG. 1 is a diagrammatic representation of the measuring section of an electrical particle sizing apparatus including the electrodes according to the prior art;

FIG. 2 is a plan view of an electrode assembly according to the invention;

FIG. 3 is a section along line III—III in FIG. 2;

FIG. 4 is a plan view of the recessed face of a block forming an inlet fluid chamber for use in cooperation with the electrode of FIG. 2;

FIG. 5 is a view from the top of the block shown in FIG. 4;

FIG. 6 is a section through another embodiment of electrode assembly of the invention having the block of FIG. 4 in position to form an inlet fluid chamber as well as a further block forming the outlet fluid chamber; and FIG. 7 is a diagrammatic representation of the flow through a measuring section during back wash rinsing of the aperture.

DETAILED DESCRIPTION

In FIG. 1 there is shown the measuring section 100 of an embodiment of the prior art. This consists of an internal vessel 101 the inside of which forms the outlet side chamber 103. The internal vessel 101 is retained within an outer vessel 102 the inside of which 105 forms the inlet side chamber. The lower end 104 of the internal vessel 101 is located below the surface of liquid in the outlet side chamber 105. Test suspension 108 is contained in the inlet chamber. In the wall 113 of the inner vessel is an aperture 106 providing fluid communication between the inlet side fluid chamber 105 and the outlet side fluid chamber 103 formed inside the inner vessel. Contact liquid 107 fills the outlet side fluid chamber.

Suspended in the liquid in the inlet side fluid chamber is inlet electrode 111, formed of a sheet of platinum and attached to lead 112. Suspended in the liquid in the outlet side fluid chamber is outlet electrode 109, of a similar construction to electrode 111 and connected to lead 110.

As shown in FIGS. 2 and 3 an electrode assembly 1 according to the invention comprises an insulator substrate 2. The substrate 2 is formed of any standard material used in the manufacture of printed circuit boards and is thus rigid and electrically insulating. A typical substrate material is epoxy coated fibreglass, commercially available material known by the designation FR-4, ceramic or polyamide.

Attached to the insulator 2 is a sheet of inert conductor (eg of platinum or gold), forming the electrode 3. The electrode 3 is substantially circular and has an external diameter of 20–25 mm. In the centre of the electrode is a hole 4 which is circular and concentric with the electrode periphery. It has a diameter of around 4 mm.

The insulator material extends under and beyond the peripheries of the electrode. Concentric with the hole within the electrode is a counterbored cavity 5 in which is retained a sapphire or ceramic component 40 through which an aperture 16 extends concentric with the electrode hole and electrode periphery. An aperture suitable for measuring red blood cells has a diameter in the range of 40 to 160 $\mu$m, preferably around 70 $\mu$m. Since the electrode is adhered directly to the insulator 2, it is unnecessary to provide additional sealing means around the edge of the hole 4 in the electrode. Additionally the entire back of the electrode may be bonded or sealed against the insulator. In some instances, however, it may be necessary to provide for a fluid tight (impermeable) seal around the periphery of the hole 4 between the substrate 2 and the electrode 3. The substrate itself is fluid tight.

The insulator 2 has four holes 6, 6', 7 and 7' located beyond the area of the electrode. These holes are for mounting of other components of the EPS apparatus, for instance the blocks forming the fluid chambers (see below).

The electrode 3 is connected via a ring of copper 8 exposed, prior to attachment of the electrode 3, at the surface of the insulator 2. Ring connector 8 is connected to lead 10 and subsequently to electrical connector 11. The electrode is also connected via ring connector 8 and lead 12 to edge connectors 13 formed on the edge of the substrate. In an alternative embodiment, the leads joining the ring connector and edge connectors may be formed as an intermediate layer of a multi-layer PCB. The edge connectors are suitable for connection to standard components. Leads 12 and 10 and the respective connectors 13 and 11 are provided to allow for alternative connection and allow flexibility in the selection of connection means. Either could be omitted.

The ring connector 8 is located at a greater distance from the centre of the electrode 3 than the external periphery of the area of the electrode which is wetted during use of the device, shown schematically by the broken line 19 in FIG. 2. By this arrangement, even if the electrode 3 is so thin that it is relatively permeable to vapour and metal, contact and possible corrosion of the electrical connectors 12, 10 and 8 is avoided since those components are distanced from the wetted area.

Through connectors 11 and/or 13 the electrode can be connected to the electronic circuitry of the EPS apparatus. The circuitry is otherwise conventional. Temperature, pressure, conductivity, pH or other physical sensors may be incorporated onto or into the board forming the electrode assembly. Such sensors may be incorporated onto or into the board and may be situated on either side of the board either in the fluid, the aperture structure or outside it. Further, the amplifier or current source, or some part of it or other related circuitry may be incorporated into or onto the board.

In FIG. 3, a section through the mid line (III—III) of the electrode assembly of FIG. 2 is shown. The first electrode 3 has hole 4 concentric with cavity 5 in the substrate 2. Furthermore on the other side of the substrate 2 is located the second electrode 14 of substantially the same size as electrode 3, electrically connected via copper ring connector 9 on the outlet side surface of the insulator to lead 17 and connector 18. The outlet electrode has a hole in its centre 15 concentric with the external periphery of electrode 14 and with cavity 5 and aperture 16 in component 40. The aperture 16 provides a passageway for fluid through the assembly.

FIGS. 4 and 5 show a view from the front and the top, respectively, of a block 20 which has a recess 21 having recess wall 41 formed in its front face. The recess forms the inlet fluid chamber with the inlet electrode of the electrode assembly. Around the periphery of the recess 21 is a groove 22 which forms a seat for a gasket. Typically the groove 22 has a total depth of around 1–2 mm, while the depth of the recess inside the inner extent of the groove 22 has a depth of around 0.4 mm.

A conduit for test suspension comprises a chamber 23 formed as a recess in the bottom face 30 of the block 20. This leads into an inlet conduit which comprises a straight diagonal passageway 25 leading from the centre of the substantially circular recess 23 to the central part 27 of the inlet fluid chamber 21.

The block is provided further with a waste outlet 29 formed in the top face 24 of the block, and joined to the recess 21 by a suspension waste conduit 31 comprising a substantially horizontal passageway 26 extending from the top of the recess 21 to a substantially vertical passageway 31 leading to the centre of the recessed outlet 29.

To optimise flow of the test suspension from the central region 27 of the recess 21 and to avoid air bubbles becoming trapped in the upper portion of the recess 21 and reducing the surface area of contact of the fluid with the electrode, there is provided a groove 28 in the recess wall 41 of a greater depth than the recess 21, for instance around 4 mm, leading vertically from the mouth of passageway 26 towards the centre of the recess.

The passageways 26, 31 and 25 typically have internal diameters of around 4 mm.

The block 20 further comprises mounting holes 32–35 located around the recess 21 which match up with holes 6, 6', 7 and 7' in the electrode assembly. The block is conveniently made of Perspex (polymethylmethacrylate), polytetrafluoroethylene, PEEK (a temperature and abrasic resistant, though non-transparent polymer) glass, ceramic or other inert material. Preferably it is transparent to allow visual inspection during operation. It can be moulded with some or all of the recesses and passageways formed in the mould or some or all of the recesses and passageways may be machined from a solid cast block.

As shown in FIG. 6, block 220, which is the same as block 20 of FIGS. 4 and 5, electrode assembly 201 and a further block 236 can be assembled together to form the measuring section of an EPS apparatus. FIG. 6 is a section along the vertical mid line of such an assemblage. In FIG. 6 the recess 223 in the bottom face of block 220 forms the chamber at the beginning of the inlet conduit. This leads into angled passageway 225 which leads into the recess 221 formed in the front face of the block 220. When in position against the inlet electrode 203, a gasket, formed by O-ring 227 is located in the groove 222 surrounding the recess 221. An outlet conduit from the inlet side fluid chamber 237 formed by recess 221 is formed by horizontal passageway 226 from the top of the recess 221 which leads into vertical passageway 231. The conduit connects the fluid inlet chamber 237 with the outlet formed by recess 229 in the top face of the block. The O-ring 227 forms a fluid tight seal against the surface of the electrode 203 of the assembly.

Retained in position against outlet electrode 214, is a second block 236. This block has a recess 239 formed in the front face positioned against the outlet electrode 214. A groove 240 formed in the front face of block 236 surrounds the recess 239. An 0 ring 241 is located in this groove to form a fluid tight seal between the block 236 and outlet electrode 214.

Inlet electrode 203 is electrically connected to copper ring connector 208 located beyond the external periphery of the inlet fluid chamber 237 formed by O ring 227. Ring connector 208 is connected to lead 210 formed as an intermediate layer in the PCB. On the outlet side, the electrode 214 is connected to copper ring connector 209, which is similar to ring connector 208, and ring connector 209 is in turn connected to embedded lead 217 and hence to connector 218. Counterbored cavity 205 in the inlet side of the insulator substrate retains a sapphire component 260 through which extends an aperture 216.

The recess 239 together with electrode 214 forms the outlet side fluid chamber 238. A contact fluid inlet conduit 242 leads from the face 244 of the block into the recess 239. A contact fluid outlet conduit 243 leads from the recess 239 through the rear face 244 of the block. The outlet 243 exits the outlet side fluid chamber 238 from a depression formed in the top internal wall of the chamber. It is so positioned as to collect and remove gas bubbles from liquid in the outlet side fluid chamber. A measured suspension waste conduit is formed by a tube 245 extending within the recess 239 with its mouth near to the aperture 216 and coaxial therewith through a passage in the back wall and face 244 of the block 236.

When the assemblage is used, a flow of suspension under test passes in the direction shown by arrow 247 into the recess 223 of the inlet side block 220. The suspension passes through conduit 225 into the inlet side fluid chamber 237. A portion of the suspension passes through aperture 216 between the electrodes 203, 214 under a pressure differential between inlet side fluid chamber 237 and outlet side fluid chamber 238. The remainder of suspension passes along suspension waste conduit 226, 231 to the outlet formed by recess 229, from which it is transferred to waste in the direction shown by the arrow.

On the outlet side of the assemblage, a flow of contact liquid passes in the direction shown by arrow 248 through conduit 242 to fill the outlet side fluid chamber 238. The contact fluid, together with any suspension which has passed through the aperture 216, is removed through either or both of the waste conduits 243 and 245. It is convenient for there to be two outlets provided since this can allow for optimisation of fluid passage through the aperture 216 and for removal of suspension from the outlet side of the aperture region and away from the electrodes, thereby minimising interference caused by cells in the electric field. The interference is further minimised by flushing (rinsing) the aperture between tests and/or by flushing during a test to remove blocked particles.

The blocks 220 and 236 are located and retained in position by bolts or other support means which pass through passageways 234 and 235 formed in the inlet block, holes 207 and 206 formed in the insulator substrate 202 and further passageways 249 and 250 formed in the outlet block (as well as the other pair of similar passageway on the other side of the assemblage). Sufficient pressure is exerted to provide adequate sealing by O-rings 227 and 241 against the electrodes.

Whilst test suspension flows through the apparatus, an electric field is set up by applying an alternating or direct current between the electrodes 203 and 214. We have found that it is convenient for the current supplied to be a direct current of between 0.1 mA and 1.0 mA. Means are provided to measure the electrical changes in the aperture 216 so that the particles may be counted and/or sized.

FIG. 7 shows a diagram of the flow during a backwash cycle. Inlet chamber 321 has sample inlet conduit 325 leading from suspension reservoir in syringe 351. Sample waste conduit 331 leads from the top of the inlet side fluid chamber. Inlet and outlet electrodes 303 and 314, respectively, provide an electric field through aperture 316 in the wall separating inlet side fluid chamber 321 and outlet side fluid chamber 338. The outlet side fluid chamber 338 is connected via inlet conduit 342 to saline reservoir in syringe 352. From the top of the outlet side fluid chamber is drip waste conduit 343 and vacuum waste conduit 345. A first valve 353 and check valve 356 are provided in suspension waste conduit 331. A second valve 354 and second check valve 357 are provided in drip waste conduit 343. A third valve 355 is provided in vacuum waste conduit 345.

In a normal cycle of the apparatus, the valves 353 to 355 and syringes 351 and 352 are operated so as to provide a higher pressure (for instance about 10 inches (25 cm) of water) between the inlet side fluid chamber 321 and the outlet side fluid chamber 338. Suspension under test is expelled from reservoir 351 through inlet side fluid chamber 321 and through the aperture 316 as well as through waste conduit 331. In a rinse cycle, or a cleaning cycle for dislodging particles lodged in the aperture 316, saline (which may be the same liquid as used for the contact liquid in the outlet side fluid chamber) is passed into the outlet side fluid chamber 338 from syringe 352, without the use of syringe 351, syringe 352 and valves 353 to 355 being adjusted so as to allow a reversed pressure differential, with a higher pressure in the outlet side fluid chamber to be achieved. This provides for a flow of saline in the opposite direction (to the service cycle) through the aperture 316. The saline flow, indicated by the arrows in FIG. 7, serves also to rinse the inlet side and outlet side fluid chambers. Further rinsing may be provided by allowing saline to be passed through inlet conduit 325 in place of suspension.

By use of the electrode assembly in which the electrodes are attached to a rigid substrate so that they cannot move relative to one another or relative to the aperture, with the aperture being very close to the electrodes such that a uniform field is produced through and around the aperture many benefits are achieved, including the following:

a) The data produced are more accurate, and more precise than with existing electrode assemblies.

b) The round electrodes match the round aperture ensuring that both the field between the electrodes and the aperture and the field inside the aperture are more uniform. A uniform field produces a more consistent voltage pulse regardless of what part of the field a cell or particle dissects.

c) The field extends minimally into the fluid body. As cells approach or exit the aperture, they distort the electrical field which disturbs the charge density inside and around the aperture and degrades the electrical signal. By minimizing the space between the electrodes and the aperture, fewer cells interrupt the field simultaneously, and those that do exert less distortion upon it as the field density decays quickly away from the aperture and electrodes. In this way, the aperture gains immunity from local movement of cells and debris.

d) The electrodes shield each other from EMI as they each have one side facing towards the other electrode. This reduces the pick up of electromagnetic interference which is dependent on the exposed surface area of the antenna (the electrodes). A further advantage of the electrodes having similar geometry and being aligned with one another is that they consequently are both exposed to very similar EMI. There is a technique (called common mode rejection) whereby the EMI noise generated on two such similar conductors is eliminated by amplifying the signal from each electrode, inverting one of the signals and then combining them. In this way, any EMI noise is cancelled. This cannot be used on freely suspended electrodes because the EMI is sufficiently different.

e) The electrodes are close to the aperture and can be smaller than typically found with EPS methods. This reduces the cost of the electrodes and their noise sensitivity.

f) The electrodes are mounted on a solid substrate. A solid substrate holds the electrodes firmly in position relative to each other, the aperture and the cells. This minimises the mechanical pick up (apertures act like microphones) by minimizing the movement of the electrodes. Additionally, free floating electrodes as are currently used, must be thick enough to sustain mechanical vibration and agitation of an automated system.

g) By mounting the electrodes on a solid substrate, the precious metal can be much thinner thereby reducing costs. Typically, the electrodes are 2 or 3 mils (50–75 $\mu$m) thick.

h) The electrode assembly can be manufactured cheaply using existing PCB manufacturing practices. As only the Pt electrodes (typically noble metals such as platinum) are exposed to the liquid, all of the interconnecting traces (and components) can be manufactured as if it were a printed circuit board. After the board is complete, two Pt discs are bonded to the surface (or otherwise applied) to form the electrodes, and soldered to make electrical connection to the rest of the board. Unlike the situation with conventional submerged electrodes, the solder joint is not exposed to liquid and is not, therefore susceptible to electrolysis or corrosion. Alternatively, the entire board can be Pt clad, and the connection traces made by etching away the unwanted Pt, much as copper PCBs are currently made. Additionally, multiple signal paths from the electrodes to the electronics increase the signal integrity.

i) The substrate can incorporate electronic or mechanical components on it. A typical substrate material is epoxy coated fibreglass, FR-4, ceramic, polyamide or other standard materials used in the manufacture of printed circuit boards (PCBs). Temperature sensors, conductivity probes, pH probes and other sensors can be mechanically and electrically connected to the substrate with a minimum of effort.

j) Shorter signal paths. By combining some or all of the components onto the substrate, the signal path between the electrodes and the amplifier is reduced to less than an inch, 25 mm, and if the amplifier is incorporated in between the electrodes, it can be reduced to millimetres (no cabling is needed).

k) The mechanical bond between the electrode and the conductor carrying the signal is not exposed to the fluid. In prior art apparatus electrodes have a piece of Pt wire welded to the electrode to carry the signal to the amplifier. As this bond occurs in the solution, it must be made of the same material to prevent corrosion. Our method limits the wetted area of the electrodes to the crosssectional area of the testing cavity, making it possible to attach the Pt electrodes to the rest of the system outside the wetted area with ordinary solder, thereby reducing costs.

l) The assembly can be quickly removed and replaced for service or experiment. The electrode assembly can be designed with an edge fitting connector, and as such can be made to fit standard connectors, such as SIMM sockets. This ensures that a gas tight connection between the assembly and the rest of the electronics. Alternatively, push fit connectors can be soldered onto the assembly.

m) The electrodes, aperture and insulator substrate always stay together. Once such an arrangement is calibrated, it produces the same results in any instrument. If several phenomena are recorded during calibration, such as temperature, pressure, pH or there are calibration curves or data, this information can be recorded and stored electronically on components on the aperture card. If the amplifier or some part of the amplifier or related circuitry is also incorporated onto the substrate, then the entire arrangement can be factory calibrated and sent to the customer ready to use without the need for further calibration. Multi-finger contact enables easy communication between the electrode assembly card and a computer to exchange data, or a code printed on the card carrying the same information.

n) The entire assembly is robust. The aperture card can be cleaned manually with a brush, in an ultrasound bath, or with chemical cleaners.

o) Service is simplified. As the electrodes snap in and out of the instrument, defective units can be replaced by the operator without the need for a service call.

p) Experimental apertures made from different materials, different size apertures, or different precious metals or conductive materials such as plastics or carbon can be easily tested. It is possible to form the aperture in the insulator which can be formed of out of a single piece of synthetic sapphire or ceramic and this avoids bonding of another component in which the aperture is formed to a cavity in a board forming the insulator. Due to the modular nature of the design, testing such alternatives is simple.

q) Flushing the apertures and rinsing the electrodes is simple, using focused jets of diluent, which also removes bubbles.

What is claimed is:

1. An electrode assembly comprising:

two flat electrodes supported in face to face relationship to one another, a plate like fluid type insulator positioned between the electrodes with the electrodes being fixed to the insulator, each electrode having a hole extending through the electrode, the holes of the two electrodes being aligned with one another, in which the insulator has a cavity which receives an initially separate element having an aperture preformed therein which has a smaller diameter than the said holes, the aperture being located such as to allow a flow of liquid to pass therethrough and through the holes in the electrode, and in which the electrodes are each joined to the insulator at the hole periphery by a fluid tight seal.

2. The measuring section of a resistive pulse spectroscopy apparatus comprising an electrode assembly according to claim 1 and an inlet side fluid chamber, one wall of which is formed by one of the electrodes and the interior of which is in fluid communication with the aperture, an inlet conduit leading into the inlet side fluid chamber, a suspension waste conduit leading out of the inlet side fluid chamber, an outlet side fluid chamber, one wall of which is formed by the other of the electrodes and the interior of which is in fluid communication with the aperture, a contact fluid conduit leading into the outlet fluid chamber, a contact fluid waste conduit leading out of the outlet fluid chamber, and a measured suspension waste conduit leading out from the outlet side fluid chamber.

3. Apparatus according to claim 2, in which the inlet side fluid chamber is formed as a recess formed in one side of a block, with the inlet and waste conduits being formed as passageways leading through from other sides of the block into the recess, the said side of the block in which the recess is formed being positioned against the respective electrode thereby forming the inlet side fluid chamber.

4. Apparatus according to claim 3, in which a fluid tight sealing gasket is provided between the face of the block having the fluid chamber forming recess and the electrode.

5. Apparatus according to claim 2, in which the outlet side fluid chamber is formed by a recess formed in one side of a block, with inlet, outlet and waste conduits formed from passageways leading from other faces of the block to the recess, the said side of the block in which the recess is formed being positioned against the respective electrode thereby forming the outlet side fluid chamber.

6. Apparatus according to claim 5, in which a gasket is provided to form a fluid tight seal between the face of the block in which the said recess is formed and the respective electrode.

7. Apparatus according to claim 4, in which the sealing gaskets and blocks are aligned on opposite sides of the electrode assembly.

8. Apparatus according to claim 3, in which the inlet side fluid chamber has a volume of less than 1 ml.

9. Assembly according to claim 1, in which the electrodes are each formed of platinum.

10. Assembly according to claim 1, in which the insulator has a thickness in the range 10 $\mu$m to 5 mm.

11. Apparatus according to claim 2, in which the operative surface area of each electrode is in the range 5 to $10^3$ mm$^2$.

12. Assembly according to claim 1, in which the insulator is a printed circuit board substrate, preferably having an amplifier connected thereto beyond the external periphery of the electrodes.

13. Assembly according to claim 1, in which the insulator extends beyond the periphery of the electrodes and in which the apertures in the electrodes and the insulator are substantially co-axial.

14. Assembly according to claim 10, in which the insulator has a thickness in the range of 0.5 to 3.0 mm.

15. Apparatus according to claim 2, in which the electrodes are each formed of platinum.

16. Apparatus according to claim 2, in which the insulator has a thickness in the range 10 $\mu$m to 5 mm.

17. Apparatus according to claim 2, in which the insulator is a printed circuit board substrate, preferably having an amplifier connected thereto beyond the external periphery of the electrodes.

18. Apparatus according to claim 2, in which the insulator extends beyond the periphery of the electrodes and in which the aperture in the electrodes and the insulator are substantially co-axial.

19. Apparatus according to claim 16, in which the insulator has a thickness in the range of 0.5 to 3.0 mm.

* * * * *